United States Patent [19]
Bank et al.

[11] Patent Number: 5,606,088
[45] Date of Patent: Feb. 25, 1997

[54] PROCESS FOR PREPARATION OF ORGANODISILANES

[75] Inventors: Howard M. Bank, Freeland; Sean P. Davern, Auburn; Binh T. Nguyen, Midland, all of Mich.

[73] Assignee: Dow Corning Corporation, Midland, Mich.

[21] Appl. No.: 623,065

[22] Filed: Mar. 28, 1996

[51] Int. Cl.$^6$ .................. C07F 7/08; C07F 7/12
[52] U.S. Cl. ............................................. 556/430
[58] Field of Search .................................. 556/430

[56] References Cited

U.S. PATENT DOCUMENTS

| | | | |
|---|---|---|---|
| 4,707,557 | 11/1987 | Nagai et al. | 556/430 |
| 4,716,240 | 12/1987 | Nagai et al. | 556/430 |
| 5,358,670 | 10/1994 | Turnbull et al. | 260/665 |

OTHER PUBLICATIONS

Semenov et al., Russian Chem. Bulletin 44:927–930, 1995.
Organometallic Compounds, Coates et al., vol. 1 pp. 76–103, (1967), Methuen and Co. LTD, London, U.K.
Encyclopedia of Chemical Technology, Kirk and Othmer, vol. 10, 721–734 (1966), The Interscience Enc, Inc., NY, NY.
Grignard Reactions of Nonmetallic Substances, Kharash et al, Prentice Hall, Inc, NY, 1954, 1306–1331.
Organic Synthesis, Turk et al., vol. 27, 7–8, 1947.

*Primary Examiner*—Paul F. Shaver
*Attorney, Agent, or Firm*—William F. Boley

[57] ABSTRACT

A one-step process for the preparation of organodisilanes. The process comprises contacting magnesium metal with a mixture comprising diethylene glycol dibutyl ether, an organic halide, and a halodisilane at a temperature within a range of about 0° C. to 250° C. The process provides a high yield of organodisilane product that is easily recoverable. The present process is especially useful for converting halodisilanes in a high-boiling mixture resulting from the direct process for making organosilane monomers into hexaorganodisilanes.

17 Claims, No Drawings

PROCESS FOR PREPARATION OF ORGANODISILANES

BACKGROUND OF INVENTION

The present invention is a one-step process for the preparation of organodisilanes. The process comprises contacting magnesium metal with a mixture comprising diethylene glycol dibutyl ether, an organic halide, and a halodisilane at a temperature within a range of about 0° C. to 250° C. The process provides a high yield of organodisilane product that is easily recoverable. The present process is especially useful for converting halodisilanes in a high-boiling mixture resulting from the direct process for making organosilane monomers into hexaorganodisilanes.

The reaction of organic halides with magnesium metal in the presence of solvents such as dialkyl ethers to form reactive complexes typically referred to as Grignard reagents is well known. The production and reactions of Grignard reagents has been the subject of books and numerous review articles. Such reviews are provided, for example, in Coates et al., *ORGANOMETALLIC COMPOUNDS*, Vol. 1, p. 76–103 (1967), Methuen and Co. LTD, London, U.K.; and in Kirk and Othmer, *ENCYCLOPEDIA OF CHEMICAL TECHNOLOGY*, Vol. 10, 721–734 (1966), The Interscience Encyclopedia, Inc., N.Y., N.Y. The structure of the Grignard reagent has not been determined with certainty. However, it is generally believed that the Grignard reagent exists as a complex in solution and solvent can play a critical role in such complex formation. The unpredictable effect of solvent on the formation and reactivity of Grignard reagents is discussed in the above cited review articles.

The reaction of Grignard reagents with halosilanes is also well known and many such reactions are described in Kharash et al., *Grignard Reactions of Nonmetallic Substances*, Prentice-Hall, Inc. N.Y., 1954, P. 1306–1331.

Turk et al., *Organic Synthesis*, Vol. 27, 7–8, 1947, teach a process for preparing 1,5 hexadiene by the reaction of allyl chloride in anhydrous ether with magnesium turnings. Turk et al. teach that this reaction results in the formation of a thick slurry which becomes unstirrable. This unstirrable slurry is then treated with a hydrochloric acid solution until the magnesium chloride by-product is in solution and the slurry becomes sufficiently fluid to be stirred.

Processes such as taught by Turk et al. are not generally acceptable as commercial processes. The formation of the non-stirrable slurry during conduct of the reaction can cause reduced mass transfer and heat transfer and therefore reduced yield of product. Furthermore, the nature of the slurry makes it necessary to treat the slurry in an additional step with a reagent to solubilize the slurry to allow isolation of the product. Typically, a major portion of the product is trapped within the non-stirrable slurry. In addition, the non-flowable nature of the slurry does not allow for the reaction to be run as a continuous process.

Semenov et al., Russian Chem. Bulletin 44:927–930, 1995, report the reaction of Grignard reagents with polychloro-substituted disilanes in tetrahydrofuran (THF) or a THF-heptane mixture.

Turnbull et al., U.S. Pat. No. 5,358,670, report the formation of alkyl Grignard reagents in diethylene glycol dibutyl ether (DEGDBE). Turnbull et al. reported that Grignard reagents prepared in the presence of DEGDBE have improved yield and stability.

It is an objective of the present invention to provide a one-step process for preparing organodisilanes using a Grignard-type reagent as an intermediate, where the process avoids many of the above discussed problems with Grignard type processes by creating a reaction mixture that is flowable and easily stirred. Thus, mass transfer and heat transfer can be improved in the reaction mixture providing for improved yield of organodisilane. In addition, the process provides for a two-phase system from which the organodisilane can be easily separated. The present process is especially useful for converting halodisilanes in a high-boiling mixture resulting from the direct process for making organosilane monomers into hexaorganodisilanes. The resulting hexaorganodisilanes can be further treated to form commercially desirable monomers such as allyltrimethylsilane.

SUMMARY OF INVENTION

The present invention is a one-step process for the preparation of organodisilanes. The process comprises contacting magnesium metal with a mixture comprising diethylene glycol dibutyl ether, an organic halide, and a halodisilane at a temperature within a range of about 0° C. to 250° C. The process provides a high yield of organodisilane product that is easily recoverable. The present process is especially useful for converting halodisilanes in a high-boiling mixture resulting from the direct process for making organosilane monomers into hexaorganodisilanes.

DESCRIPTION OF INVENTION

The present invention is a one-step process for the preparation of organodisilanes. The process comprises contacting magnesium metal with a mixture comprising diethylene glycol dibutyl ether, an organic halide described by formula

$$R^1X,$$

and a halodisilane described by formula

$$R^2{}_aSi_2X_{6-a}$$

at a temperature within a range of about 0° C. to 250° C.; where $R^1$ is a monovalent hydrocarbon radical comprising about one to 20 carbon atoms, each $R^2$ is an independently selected monovalent hydrocarbon radical comprising about one to 20 carbon atoms, X is a halogen atom selected from a group consisting of bromine and chlorine, and a=0 to 5.

In the present process, by the term "one-step" it is meant that it is not necessary to isolate an intermediate Grignard type reagent in the process and further react this Grignard type reagent with the halodisilane to form the organodisilane. Furthermore, it is not necessary to conduct a separate solubilization step on the resulting product mixture to facilitate recovery of the organodisilane.

The process comprises reacting magnesium metal with an organic halid in the presence of a halodisilane and diethylene glycol dibutyl ether (DEGDBE). The method of preparing the magnesium metal and the physical form of the magnesium metal can be any of those known in the art. The magnesium metal can be, for example, in the form of powder, chips, or shavings. A preferred form of magnesium metal is in the form of shavings.

Contact of the magnesium metal with the organic halide can be effected in standard reactors suitable for running Grignard type reactions. The reactor can be of a batch type, semi-batch type, or continuous-type. A preferred reactor is a continuous-type reactor. The environment in which the present process is run should be inert. Therefore, in a preferred process the reactor is purged and blanketed with an inert gas such as, for example, nitrogen or argon.

The mole ratio of magnesium to organic halide fed to the reactor is not critical and can be varied within wide limits. In a batch process it is preferred that the mole ratio of magnesium to organic halide provide organic halide in sufficient excess to ensure essentially total conversion of the magnesium to magnesium salts. When the present process is conducted as a continuous process, the magnesium metal is typically present in excess in relation to the organic halide fed to the reactor. In such a case, the rate of feed of organic halide and halodisilane to the reactor can be controlled to assure acceptable levels of conversion of the organic halide to the organodisilane and minimal presence of unreacted organo magnesium halide complexes. The halodisilane feed may be split, with a portion being added after the magnesium bed to insure complete reaction of the organo magnesium halide complex. Excess organic halide and halodisilane added to the reactor can be recovered and recycled to the process.

Organic halides useful in the present method are described by formula $R^1X$, where $R^1$ is a monovalent hydrocarbon radical comprising about one to 20 carbon atoms and X is a halogen selected from a group consisting of bromine and chlorine. $R^1$ can be, for example, an alkyl such as methyl, ethyl, propyl, tert-butyl, and eicosyl; a cycloalkyl such as cyclopentyl and cyclohexyl; an alkenyl such as vinyl, allyl, and hexenyl; a cycloalkenyl such as pentenyl and hexenyl; an aryl such as phenyl, tolyl, and naphthyl; and an aralkyl such as benzyl, beta-phenylethyl, and gamma-tolylpropyl. Preferred is when $R^1$ is methyl. Preferred is when the halogen substituent of the organic halide is chlorine. The preferred organic halide is methyl chloride.

Halodisilanes useful in the present process are described by formula $R^2_aSi_2X_{6-a}$, where each $R^2$ is an independently selected monovalent hydrocarbon radical comprising about one to 20 carbon atoms, X is a halogen selected from a group consisting of bromine and chlorine, and a=0 to 5. $R^2$ can be, for example, an alkyl such as methyl, ethyl, propyl, tert-butyl, and eicosyl; a cycloalkyl such as cyclopentyl and cyclohexyl; an alkenyl such as vinyl, allyl, and hexenyl; a cycloalkenyl such as pentenyl and hexenyl; an aryl such as phenyl, tolyl, and naphthyl; and an aralkyl such as benzyl, beta-phenylethyl, and gamma-tolylpropyl. Preferred is when $R^2$ is methyl. Preferred is when the halogen substituent of the halodisilane is chlorine. The preferred halodisilane is selected from a group consisting of 1,2-dimethyl-1,1,2,2-tetrachlorodisilane, 1,1,2-trimethyl-1,2,2-trichlorosilane, 1,1,2,2-tetramethyl-1,2-dichlorodisilane, and 1,1,1,2-tetramethyl-2,2-dichlorodisilane.

The present process is especially useful for converting halodisilanes in a high-boiling mixture resulting from the direct process for making organosilane monomers into hexaorganodisilanes. The so called "direct process" for making organosilanes involves the contact of an organic halide with elemental silicon in the present of suitable catalysts at a temperature of about 300° C. to 350° C. Typically during conduct of the direct process gaseous products, unreacted organic halide, and fine particulates are continuously removed from the process. The removed materials are subsequently distilled to recover monosilanes, leaving a high-boiling mixture comprising halodisilanes. This high-boiling mixture has limited commercial value and therefore it is desirable to convert it to more useful monosilanes. The present process can convert the halodisilanes into organodisilanes and preferably into hexaorganodisilanes which can then be cleaved by standard methods to form organosilane monomers. A preferred halodisilane containing high-boiling mixture for use in the present process is one with a boiling point above about 70° C. resulting from the distillation of monosilanes from the reaction product of methyl chloride with elemental silicon. Such a high-boiling mixture may comprising as much as 50 to 60 weight percent halodisilanes. A typical composition for such a halodisilane containing high-boiling mixture is described, for example, in Ferguson et al., U.S. Pat. No. 5,430,168, which is incorporated by reference for its teaching of such compositions. In some instances, it may be desirable to pre-treat the high-boiling mixture by a process such as filtration to remove particulates.

The mole ratio of organic halide to halodisilane can be varied within a range of about 0.1 to 10 moles of organic halide per each mole of halogen substituted on the silicon atoms of the halodisilane. Preferred is when the mole ratio of organic halide to halodisilane is within a range of about 1 to three moles of organic halide per each mole of halogen substituted on the silicon atoms of the halodisilane. In a preferred process the magnesium is added to the process in excess to the organic halide forming an organo magnesium halide intermediate. In such a preferred process the preferred mole ratio of halogen substituted on the silicon atoms of the halodisilane to the organic magnesium halide intermediate is less than one.

The present process is conducted in the presence of diethylene glycol dibutyl ether (DEGDBE). About one to fifteen moles of DEGDBE can be added to the process per mole of organic halide. Preferred is when about three to ten moles of DEGDBE is added to the process per mole of organic halide. Even more preferred is when about 1.5 to five moles of DEGDBE is added to the process per mole of organic halide.

The present process can be run at a temperature within a range of about 0° C. to 250° C. It is preferred that the present process be run at a temperature within a range of about 30° C. to 170° C. The pressure at which the present process is run is not critical and can be ambient to about 200 psig. A preferred pressure is within a range of from about 0 psig to 125 psig.

The product of the present process is an organodisilane where one or more of the halogen atoms substituted on the silicon atoms of the halodisilane are replaced with an organic substituent. Those skill in the art will recognize that the amount of such substitution can be controlled, for example, by controlling the ratio of the moles of organic halide to the moles of halogen substituted on the silicon atoms of the halosilanes. For example, the present process can be conducted with the ratio of the number of moles of organic halide to moles of halide substituted on the silicon atoms of the halodisilane being greater than about 1:1 and with a=0 to 4.

The preferred product of the present process is a hexaorganodisilane, where all of the halogen substituents on the silicon atoms of the halodisilane have been replaced by an organic group. The preferred hexaorganodisilane prepared by the present process is hexamethyldisilane.

The mixture resulting from conduct of the present process on standing separates into two-phases, with one phase comprising the organodisilane in DEGDBE and the other phase comprising a magnesium dihalide complex solubilized in DEGBDE. The organodisilane can be separated from the DEGDBE by, for example, distillation. The DEGDBE may be recovered from one or both of these phases and recycled to the method.

The following example is provided to illustrate the present invention. The example is not intended to limit the scope of the present claims.

Example 1. The reaction of magnesium metal, methyl chloride, and methylchlorodisilanes containing high-boiling mixture resulting from a direct process for making methylsilanes, in diethylene glycol dibutyl ether (DEGDBE) was evaluated. The halodisilane content of the high-boiling mixture is provided in Table 1. Magnesium turnings (0.41 mol), DEGDBE (1.24 mol), and 30.7 g of the high-boiling mixture described in Table 1 were loaded into a glass flask equipped with a reflux condenser, addition funnel, air stirrer, heating mantle, and nitrogen inlet port. The flask was purged with nitrogen and then heated to 85° C. Methyl chloride was then sparged into the reactor until the magnesium was consumed. An exotherm was observed, with the temperature rising to about 130° C. The reaction mixture was cooled in an ice bath to a temperature of about 85° C. and stirring continued for an additional 3.5 hours. As the reaction proceeded the reaction mixture was observed to separate into two-phases. The reaction mixture was transferred to a separatory funnel and allowed to cool and separate into two-phases. The top-phase was analyzed by gas chromatography using a flame ionization detector (GC-FID) and found to comprising 9.4 area % hexamethyldisilane (area %= percent of total area under the GC-FID trace), 84 area % DEGBDE, and a minor amount of tetramethylsilane. No unreacted methylchlorodisilanes were detected in the top-phase.

TABLE 1

| Halodisilane Composition of High-Boiling Mixture | |
|---|---|
| Halodisilane | GC-FID Area % |
| $MeCl_2SiSiMeCl_2$ | 24.7 |
| $Me_2ClSiSiMeCl_2$ | 25.4 |
| $Me_2ClSiSiMe_2Cl$ | 11.6 |
| $Me_3SiSiMeCl_2$ | 2.8 |

We claim:

1. A one-step process for preparation of organodisilanes, the process comprising contacting magnesium metal with a mixture comprising diethylene glycol dibutyl ether, an organic halide described by formula $$R^1X,$$

and a halodisilane described by formula $$R^2{}_aSi_2X_{6-a}$$

at a temperature within a range of about 0° C. to 250° C.; where $R^1$ is a monovalent hydrocarbon radical comprising about one to 20 carbon atoms, each $R^2$ is an independently selected monovalent hydrocarbon radical comprising about one to 20 carbon atoms, X is a halogen atom selected from a group consisting of bromine and chlorine, and a=0 to 5.

2. A process according to claim 1, where the process is conducted as a continuous process in a continuous-type reactor.

3. A process according to claim 1, where $R^1$ is methyl.

4. A process according to claim 1, where X is chlorine.

5. A process according to claim 1, where the organic halide is methyl chloride.

6. A process according to claim 1, where $R^2$ is methyl.

7. A process according to claim 1, where the halodisilane is selected from a group consisting of 1,2-dimethyl-1,1,2,2-tetrachlorodisilane, 1,1,2-trimethyl-1,2,2-trichlorodisilane, 1,1,2,2-tetramethyl-1,2-dichlorodisilane, and 1,1,1,2-tetramethyl-2,2-dichlorodisilane.

8. A process according to claim 1, where the halosilane comprises a component of a high-boiling mixture having a boiling point above about 70° C., the high-boiling mixture resulting from the distillation of monosilanes from the reaction product of methyl chloride with elemental silicon.

9. A process according to claim 1, where the mole ratio of organic halide to halodisilane is within a range of about 0.1 to 10 moles of organic halide per each mole of halogen substituted on silicon atoms of the halodisilane.

10. A process according to claim 1, where the mole ratio of organic halide to halodisilane is within a range of about one to three moles of organic halide per each mole of halogen substituted on the silicon atoms of the halodisilane.

11. A process according to claim 1, where the mixture comprises about one to 15 moles of diethylene glycol dibutyl ether per mole of organic halide.

12. A process according to claim 1, where the mixture comprises about 1.5 to five moles of diethylene glycol dibutyl ether per mole of organic halide.

13. A process according to claim 1, where the temperature is within a range of about 30° C. to 170° C.

14. A process according to claim 1, where the contacting is conducted under a pressure of about 0 psig to 125 psig.

15. A process according to claim 1, where the product of the process is a hexaorganodisilane.

16. A process according to claim 15, where the hexaorganodisilane is hexamethyldisilane.

17. A one-step process for preparation of hexamethyldisilane, the process comprising contacting magnesium metal with a mixture comprising methyl chloride, about 1.5 to five moles of diethylene glycol dibutyl ether per mole of methyl chloride; and a high-boiling mixture having a boiling point above about 70° C. resulting from the reaction of methyl chloride with elemental silicon, where the high-boiling mixture comprises a halodisilane described by formula $$Me_aSi_2Cl_{6-a}$$

at a temperature within a range of about 30° C. to 170° C.; where Me represents methyl, a=0 to 5, and the mole ratio of methyl chloride to halosilane is within a range of about one to three moles of methyl chloride per each mole of chlorine substituted on the silicon atoms of the halodisilane.

* * * * *